United States Patent
Kim et al.

(10) Patent No.: US 10,453,642 B2
(45) Date of Patent: Oct. 22, 2019

(54) CHARGED PARTICLE GENERATION DEVICE AND TARGET UNIT

(71) Applicant: ELECTRONICS AND TELECOMMUNICATIONS RESEARCH INSTITUTE, Daejeon (KR)

(72) Inventors: Jinsun Kim, Daejeon (KR); Moon Youn Jung, Daejeon (KR)

(73) Assignee: ELECTRONICS AND TELECOMMUNICATIONS RESEARCH INSTITUTE, Daejeon (KR)

( * ) Notice: Subject to any disclaimer, the term of this patent is extended or adjusted under 35 U.S.C. 154(b) by 0 days.

(21) Appl. No.: 16/128,248

(22) Filed: Sep. 11, 2018

(65) Prior Publication Data

US 2019/0080874 A1 Mar. 14, 2019

(30) Foreign Application Priority Data

Sep. 11, 2017 (KR) .................. 10-2017-0116153
Aug. 3, 2018 (KR) .................. 10-2018-0090939

(51) Int. Cl.
*H01J 27/24* (2006.01)
*A61N 5/10* (2006.01)
*H01J 27/02* (2006.01)

(52) U.S. Cl.
CPC .............. *H01J 27/24* (2013.01); *A61N 5/10* (2013.01); *A61N 5/1077* (2013.01); *H01J 27/022* (2013.01); *A61N 2005/1087* (2013.01); *A61N 2005/1088* (2013.01)

(58) Field of Classification Search
USPC ........................................ 250/492.24, 423 P
See application file for complete search history.

(56) References Cited

U.S. PATENT DOCUMENTS

| 8,835,870 | B2 | 9/2014 | Jung et al. |
| 8,872,140 | B2 | 10/2014 | Jung et al. |
| 9,024,274 | B2 | 5/2015 | Jung et al. |
| 9,117,619 | B2 | 8/2015 | Shin et al. |
| 9,656,100 | B2 | 5/2017 | Jung et al. |
| 10,056,221 | B2 | 8/2018 | Jung et al. |

(Continued)

FOREIGN PATENT DOCUMENTS

| KR | 10-2013-0081631 A | 7/2013 |
| KR | 10-2015-0129959 A | 11/2015 |
| KR | 10-2015-0129961 A | 11/2015 |

OTHER PUBLICATIONS

Yu Chen et al., "ZnO single butterfly wing scales: synthesis and spatial optical anisotropy", Journal of Materials Chemistry, 2011, pp. 6140-6143, vol. 21, The Royal Society of Chemistry.

*Primary Examiner* — Kiet T Nguyen

(57) ABSTRACT

Provided is a charged particle generation device. The charged particle generation device includes a light source unit configured to emit a laser, a target layer that receives the laser and emits charged particles, and a focusing structure disposed on the target layer to focus the laser. The focusing structure includes solid films extending on an upper surface of the target layer in a direction away from the target layer, and a pore section disposed between the solid films and having a porous structure. The focusing structure includes a material having a higher atomic number than carbon.

11 Claims, 11 Drawing Sheets

(56) References Cited

U.S. PATENT DOCUMENTS

2002/0090194 A1* 7/2002 Tajima .................. G21K 1/003
    385/147
2013/0158632 A1 6/2013 Park et al.
2013/0261369 A1 10/2013 Jung et al.

* cited by examiner

CHARGED PARTICLE GENERATION DEVICE AND TARGET UNIT

CROSS-REFERENCE TO RELATED APPLICATIONS

This U.S. non-provisional patent application claims priority under 35 U.S.C. § 119 of Korean Patent Application No. 10-2017-0116153, filed on Sep. 11, 2017, and 10-2018-0090939 filed on Aug. 3, 2018, the entire contents of which are hereby incorporated by reference.

BACKGROUND

The present disclosure herein relates to a charged particle generation device and a target unit, and more particularly, to a charged particle generation device and a target unit having improved charged particle generation efficiency.

Unlike X-ray or gamma ray treatment methods, since charged particle treatment methods may accurately attack cancer cells while minimizing damage to normal tissues, they are attracting attention as patient-friendly treatments. However, in relation to the currently used charged particle therapy device, since the size of the charged particle generation device is huge and the equipment is expensive to construct and operate, as a method of generating charged particles using a high-power pulse laser is proposed, it is expected that the size and price of the treatment device will be greatly reduced.

To develop a competitive laser ion accelerator for tumor therapy, a medical device is developed to treat the deep part of the body with the energy of the charged particle generated. However, most of the methods are currently being studied to increase the intensity of the laser light source to generate high energy charged particles.

SUMMARY

The present disclosure is to provide a charged particle generation device and target unit with improved charged particle generation efficiency.

The present disclosure is to provide a charged particle generation device and target unit that increase the energy of charged particles at low cost.

An embodiment of the inventive concept provides a charged particle generation device including: a light source unit configured to emit a laser; a target layer that receives the laser and emits charged particles; and a focusing structure disposed on the target layer to focus the laser, wherein the focusing structure includes: solid films extending on an upper surface of the target layer in a direction away from the target layer; and a pore section disposed between the solid films and having a porous structure, wherein the focusing structure includes a material having a higher atomic number than carbon.

In an embodiment, the focusing structure may include aluminum (Al) or zinc (Zn).

In an embodiment, the focusing structure may further include a metal film surrounding the solid films and the pore section, wherein the metal film may include a material having a higher atomic number than carbon.

In an embodiment, the solid films may be arranged along a first direction parallel to the upper surface of the target layer and each of the solid films may extend in a second direction intersecting with the first direction.

In an embodiment, the pore section may include a plurality of pores and a boundary layer surrounding the pores, and the boundary layer may have a mesh shape.

In an embodiment, the pore section may include a plurality of pores and a boundary layer surrounding the pores, wherein the boundary layer may include first sub-boundary layers and second sub-boundary layers each protruding from one side wall and the other side wall of each of the solid films, wherein the first sub-boundary layers may be arranged in a third direction perpendicular to the upper surface of the target layer, wherein the second sub-boundary layers may be arranged in the third direction, and each of the second sub-boundary layers may be disposed between the first sub-boundary layers.

In an embodiment of the inventive concept, a target unit includes: a target layer having a first surface for receiving a laser and a second surface for emitting charged particles; solid films extending from the first surface of the target layer in a direction away from the target layer; and a pore section disposed between the solid films and having a porous structure, wherein the solid films may be arranged along a first direction parallel to the first surface of the target layer, each of the solid films extending in a second direction intersecting with the first direction, wherein the solid films and the pore section may include a material having a higher atomic number than carbon.

In an embodiment, the solid films and the pore section may include aluminum (Al) or zinc (Zn).

In an embodiment, the target unit may further include a metal film surrounding the solid films and the pore section, wherein the metal film may include a material having a higher atomic number than carbon.

In an embodiment, the pore section may include a mesh-shaped boundary layer connecting two solid films adjacent to each other among the solid films and a plurality of pores defined by the boundary layer.

In an embodiment, the solid films may include a first solid film and a second solid film adjacent to each other, wherein the pore section may include first sub-boundary layers protruding from the first solid film toward the second solid film and second sub-boundary layers protruding from the second solid film toward the first solid film, wherein the first sub-boundary layers and the second sub-boundary layers may be alternately arranged along a direction away from the target layer.

BRIEF DESCRIPTION OF THE FIGURES

The accompanying drawings are included to provide a further understanding of the inventive concept, and are incorporated in and constitute a part of this specification. The drawings illustrate exemplary embodiments of the inventive concept and, together with the description, serve to explain principles of the inventive concept. In the drawings.

DETAILED DESCRIPTION

Figure 1:
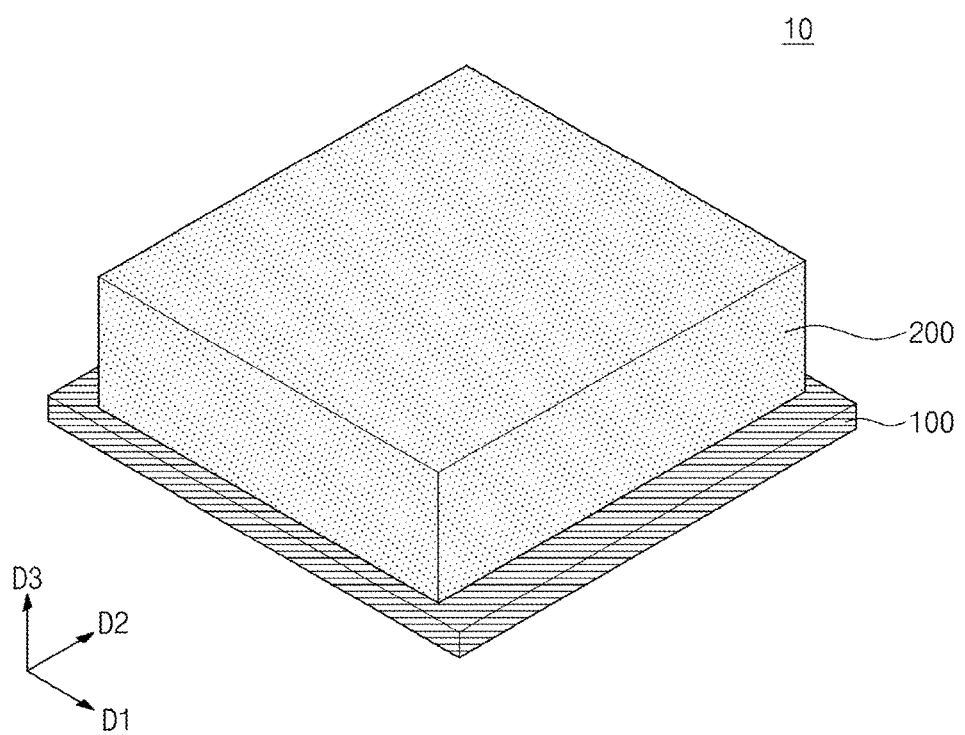
FIG. 1 is a perspective view of a target unit of a charged particle generation device according to exemplary embodiments of the inventive concept.

In order to fully understand the configuration and effects of the technical spirit of the inventive concept, preferred embodiments of the technical spirit of the inventive concept will be described with reference to the accompanying drawings. However, the technical spirit of the inventive concept is not limited to the embodiments set forth herein and may be implemented in various forms and various modifications may be applied thereto. Only, the technical spirit of the inventive concept is disclosed to the full through the description of the embodiments, and it is provided to those skilled in the art that the inventive concept belongs to inform the scope of the inventive concept completely.

Like reference numerals refer to like elements throughout the specification. Embodiments described in this specification will be described with perspective views and/or conceptual views, that is, ideal exemplary views of the inventive concept. In the drawings, the thicknesses of areas are exaggerated for effective description. Areas exemplified in the drawings have general properties, and are used to illustrate a specific shape of a semiconductor package region. Thus, this should not be construed as limited to the scope of the inventive concept. It will be understood that various terms are used herein to describe various components but these components should not be limited by these terms. These terms are just used to distinguish a component from another component. Embodiments described herein include complementary embodiments thereof.

The terms used in this specification are used only for explaining specific embodiments while not limiting the inventive concept. The terms of a singular form may include plural forms unless referred to the contrary. The meaning of "comprises," and/or "comprising" in this specification specifies the mentioned component but does not exclude at least one another component.

Hereinafter, preferred embodiments of the technical spirit of the inventive concept are described with reference to the accompanying drawings so that the inventive concept is described in more detail.

FIG. 1 is a perspective view of a target unit of a charged particle generation device according to exemplary embodiments of the inventive concept.

Referring to FIG. 1, a target unit 10 of a charged particle generation device including a target layer 100 and a focusing structure 200 provided on the target layer 100 may be provided. In exemplary embodiments, the target layer 100 may receive a laser to emit a charged particle. For example, the charged particle may be a cation and/or a proton. For example, when the target layer 100 is a thin film containing carbon (C), carbon cations may be emitted from the target layer 100. However, the target layer 100 emits charged particles by way of example. In other exemplary embodiments, the target layer 100 may emit radiation (e.g., X-rays). The target layer 100 may have a first surface on which the focusing structure 200 is disposed and a second surface opposite the first surface. The target layer 100 may receive a laser at the first surface and emit charged particles to the second surface.

The focusing structure 200 may be a porous film. For example, the focusing structure 200 may include pores (not shown) and boundary layers (not shown) surrounding the pores therein. Exemplary structures of the focusing structure 200 are described below.

The focusing structure 200 may be converted into a plasma layer (not shown) by irradiation of a laser (not shown). For example, a laser may be irradiated to the focusing structure 200 having a solid state to vaporize the focusing structure 200. A focusing structure having a gaseous state may receive energy from the laser and be ionized and converted into a plasma layer. In this case, the focusing structure 200 may change to a plasma state. The plasma layer may contain free electrons and ions therein.

Depending on the ratio of the boundary layers in the focusing structure 200, the free electrons of the plasma layer may be distributed to have a near-critical electron density. The near-critical electron density may be an electron density having a value close to the critical electron density. The critical electron density is the density of free electrons when the frequency of the electromagnetic wave generated by the free electrons in the plasma is equal to the frequency of the plasma. For example, near-critical electron density may have a value less than critical electron density but greater than 0.7 times the critical electron density, or may have a value greater than the critical electron density but less than three times the critical electron density. When the free electrons of the plasma layer have a near-critical electron density, the laser may be focused while passing through the plasma layer.

When the ratio of the boundary layers in the focusing structure 200 is too high or the focusing structure 200 is filled with the boundary layers, the density of free electrons in the plasma layer may be greater than the critical electron density. When the laser is irradiated onto a plasma layer having a larger electron density than a near-critical electron density, the laser may be reflected without passing through the plasma layer. Thus, the laser may not be focused.

If the ratio of the boundary layer is too low, the density of free electrons in the plasma layer may be less than the near-critical electron density. When the laser is irradiated onto a plasma layer having a smaller electron density than the near-critical electron density, the laser may pass through the plasma layer as it is. That is, the laser may not be focused while passing through the plasma layer. Thus, the laser may not be focused.

The boundary layer may be uniformly distributed within the focusing structure 200. Thus, the free electrons in the plasma layer may be uniformly distributed. As the free electrons are uniformly distributed, the focusing speed of the laser passing through the plasma layer may be increased. Accordingly, the focusing structure 200 according to the inventive concept may maximize the focusing of the laser.

The magnitude of the energy of charged particles emitted from the target layer 100 may be proportional to the intensity of the laser. Generally, in order to increase the intensity of the laser, a method of increasing the output of the laser may be used. However, increasing the laser output requires high cost.

The focusing structure 200 according to the inventive concept may focus a laser and provide the laser to the target layer 100. Since the intensity of the laser is inversely proportional to the irradiation area of the laser, when the laser is focused, the intensity of the laser may be increased. Thus, the target layer 100 receiving the focused laser may emit charged particles (e.g., protons or cations) with high energy.

Figure 2:
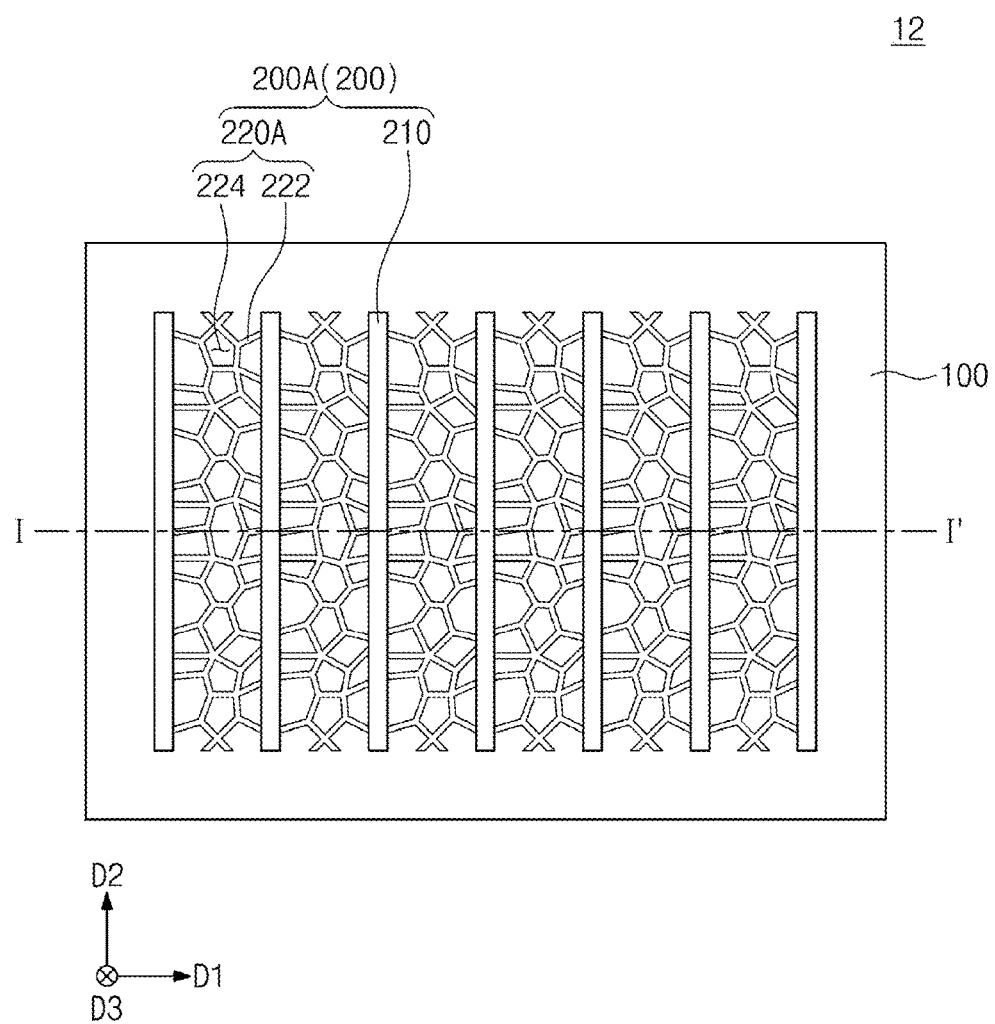
FIG. 2 is a plan view of a target unit of a charged particle generation device according to exemplary embodiments of the inventive concept.
Figure 3:
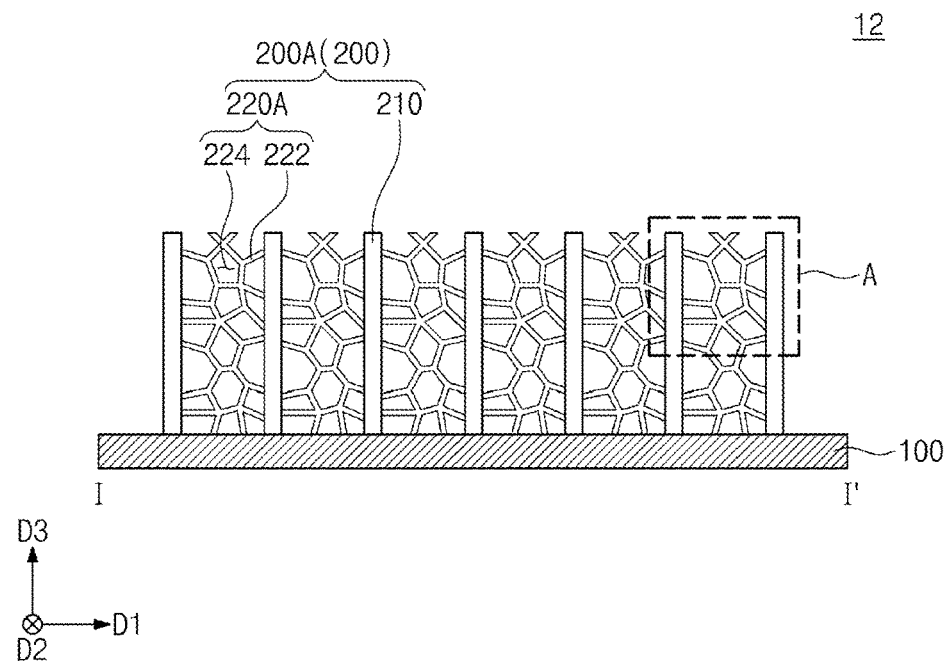
FIGS. 3 and 5 are cross-sectional views of the target unit of a charged particle generation device according to exemplary embodiments of the inventive concept, and correspond to I to I' portions of FIG. 2.
Figure 4:
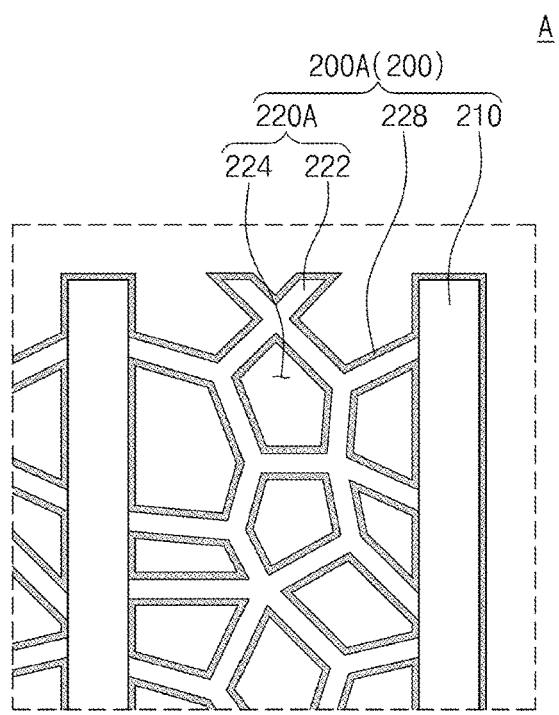
FIGS. 4 and 6 are enlarged cross-sectional views of a charged particle generation device according to exemplary embodiments of the inventive concept and correspond to a portion A of FIG. 3 and a portion B of FIG. 5, respectively.
Figure 5:
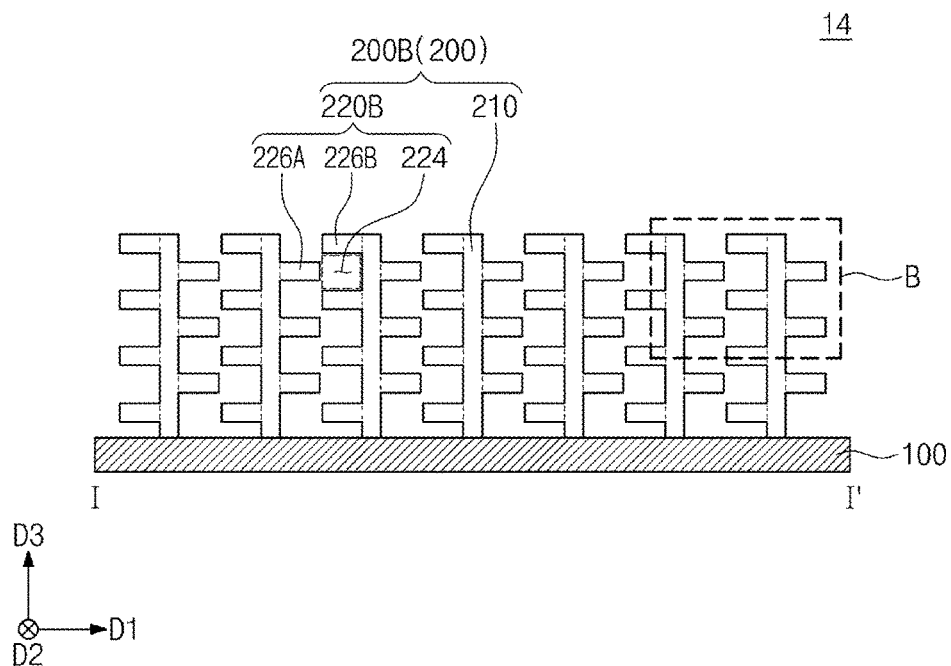
Figure 6:
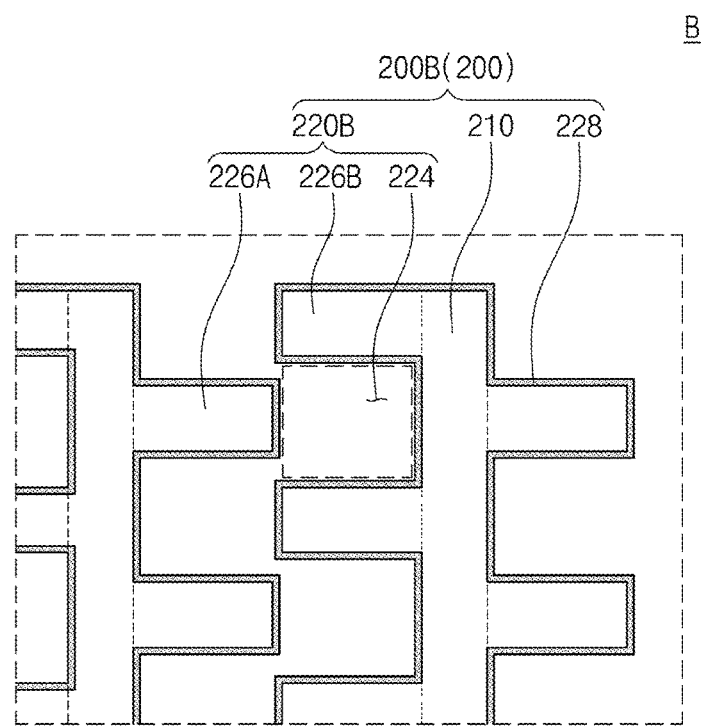

FIG. 2 is a plan view of a target unit of a charged particle generation device according to exemplary embodiments of the inventive concept. FIGS. 3 and 5 are cross-sectional views of the target unit of a charged particle generation device according to exemplary embodiments of the inventive concept, and correspond to I to I' portions of FIG. 2. FIGS. 4 and 6 are enlarged cross-sectional views of a charged particle generation device according to exemplary embodiments of the inventive concept and correspond to a portion A of FIG. 3 and a portion B of FIG. 5, respectively. For conciseness of description, contents substantially identical to the contents described with reference to FIG. 1 are not described.

Referring to FIGS. 2 and 3, a target unit 12 of a charged particle generation device, which includes a target layer 100 and a first focusing structure 200A or 200 on the target layer 100, may be provided. The target layer 100 may be substantially the same as the target layer described with reference to FIG. 1. The first focusing structure 200A or 200 may correspond to the focusing structure 200 described with reference to FIG. 1.

The first focusing structure 200A or 200 may include solid films 210 and first pore sections 220A alternately and repeatedly disposed along the first direction D1 parallel to the upper surface of the target layer 100. The solid films 210 may be arranged in a first direction D1. The solid films 210 may extend on the target layer 100 in the third direction D3. The solid films 210 may not include pores therein. That is, the solid films 210 may be filled with materials constituting the solid films 210. The solid films 210 may extend in a second direction D2 parallel to the upper surface of the target layer 100 and intersecting the first direction D1. The width of each of the solid films 210 may be constant. The width may be a distance along the first direction D1 between the both side walls of each of the solid films 210. However, this is an exemplary one. In other exemplary embodiments, each of the solid films 210 may have tapered sidewalls away from the target layer 100. That is, the width of each of the solid films 210 may become smaller as the distance from the target layer 100 increases.

The first pore sections 220A may be arranged in a first direction D1. The first pore sections 220A may be interposed between the solid films 210, respectively. Each of the first pore sections 220A may include a porous film. Each of the first pore sections 220A may include a boundary layer 222 and pores 224 surrounded by the boundary layer 222. The boundary layer 222 may correspond to the boundary layer described with reference to FIG. 1. The boundary layer 222 may extend in a random direction. That is, the extending direction of the boundary layer 222 may not be specified. The boundary layer 222 may have a mesh shape. However, the shape of the boundary layer 222 shown in FIGS. 2 and 3 is exemplary. The boundary layer 222 may be uniformly distributed within each of the first pore sections 220A. For example, the boundary layer 222 may not be densely packed at the lower part or upper part of each of the first pore sections 220A. Although the boundary layers 222 in the first pore sections 220A are shown as having the same shapes, this is exemplary.

The first focusing structure 200A or 200 may include a material having an atomic number higher than carbon. The first focusing structure 200A or 200 may include, for example, aluminum (Al), titanium (Ti), silicon (SiO2), or zinc (Zn). As the first focusing structure 200A or 200 includes a material having an atomic number higher than carbon, the energy of charged particles generated from the target unit 10 may be increased.

In exemplary embodiments, the first focusing structure 200A or 200 may be formed using a pulse laser deposition process, a foam sintering process, a sol-gel process, or a self-assembly process.

In the exemplary embodiments, the first focusing structure 200A or 200 may be extracted from the natural object. For example, the first focusing structure 200A or 200 may be extracted from a wing of a tiger butterfly. For example, the epidermis of the wing of a tiger butterfly may have a shape similar to that of the first focusing structure 200A or 200. Therefore, the skin portion may be extracted from the wing of the tiger butterfly and used as the first focusing structure 200A or 200. Forming the first focusing structure 200A or 200 may include extracting the pre-focusing structure from the natural object and performing a process of changing the material of the pre-focusing structure. The process of modifying the material of the pre-focusing structure may be, for example, an anodic oxidation process. For example, the first focusing structure 200A or 200 may include $Al_2O_3$, $TiO_2$, $SiO_2$, and ZnO.

When the first focusing structure 200A or 200 is irradiated with a laser, the first focusing structure 200A or 200 may be converted into a plasma layer (not shown). The free electrons in the plasma layer may have a near-critical electron density. Thus, the laser may pass through the plasma and may be focused.

The boundary layers 222 are uniformly distributed in the first focusing structure 200A or 200 to uniformly distribute the free electrons in the plasma layer. Thus, the laser may be focused to the maximum.

In the exemplary embodiments, as shown in FIG. 4, the first focusing structure 200A or 200 may further include a metal film 228 covering the first pore sections 220A and the boundary layer 222. The metal film 228 may include a material having an atomic number higher than carbon. The metal film 228 may include, for example, gold (Au) or silver (Ag). The metal film 228 may increase the energy of charged particles generated by reducing the movement of the elements in the first focusing structure 200A or 200 when charged particles are generated.

FIG. 5 is a front view of a target unit of a charged particle generation device in exemplary embodiments of the inventive concept. For conciseness of description, contents substantially identical to the contents described with reference to FIGS. 1 to 4 are not described.

Referring to FIG. 5, a target unit 14 of a charged particle generation device, which includes a target layer 100 and a second focusing structure 200B or 200 on the target layer 100, may be provided. The target layer 100 may be substantially the same as the target layer described with reference to FIGS. 2 and 3.

The second focusing structure 200B or 200 may include solid films 210 and second pore sections 220B alternately and repeatedly disposed along the first direction D1. The solid films 210 may be substantially the same as those described with reference to FIGS. 2 and 3.

Each of the second pore sections 220B may include a porous film. Each of the second pore sections 220B may include first sub-boundary layers 226A projecting in a first direction D1 from one side wall of each of the solid films 210. Although the lengths of the first sub-boundary layers 226A along the first direction D1 are shown to be equal to each other, this is exemplary. In other exemplary embodiments, the length of the first sub-boundary layers 226A may be greater toward the target layer 100. The first sub-boundary layers 226A may be spaced apart from each other in a third direction D3 intersecting the upper surface of the target layer 100 on the target layer 100. For example, the first sub-boundary layers 226A may be arranged at equal intervals along the third direction D3. The first sub-boundary layers 226A may extend in the second direction D2.

Each of the second pore sections 220B may include second sub-boundary layers 226B projecting in a direction opposite to the first direction D1 from the each opposite side wall of the solid films 210. Although the lengths of the second sub-boundary layers 226B along the first direction D1 are shown to be equal to each other, this is exemplary. In other exemplary embodiments, the length of the second sub-boundary layers 226B may be greater toward the target layer 100. The second sub-boundary layers 226B may be spaced apart from each other in a third direction D3 intersecting the upper surface of the target layer 100. For example, the second sub-boundary layers 226B may be arranged at equal intervals along the third direction D3. The second sub-boundary layers 226B may extend in the second direction D2.

In other words, the second pore sections 220B may include a first solid film and a second solid film adjacent to each other. The first sub-boundary layers 226A may protrude from the first solid film toward the second solid film. The second sub-boundary layers 226B may protrude from the second solid film toward the first solid film.

The first and second sub-boundary layers 226A and 226B may be arranged in a zigzag manner along the third direction D3. In other words, the first and second sub-boundary layers 226A and 226B may be alternately arranged in the direction away from the target layer 100. For example, each of the second sub-boundary layers 226B may be disposed between first sub-boundary layers 226A immediately adjacent to each other. The first and second sub-boundary layers 226A and 226B may not be horizontally overlapped with each other. However, this is an exemplary one. The first and second sub-boundary layers 226A and 226B may not vertically overlap each other. However, this is an exemplary one. The number of the first and second sub-boundary layers 226A, 226B is illustratively shown. The first and second sub-boundary layers 226A and 226B may be uniformly distributed within each of the second pore sections 220B. For example, the first and second sub-boundary layers 226A and 226B may not be densely packed in the lower part or upper part of each of the second pore sections 220B.

Pores 224 may be disposed between the first and second sub-boundary layers 226A and 226B. The shape of the pores 224 may be defined by the first and second sub-boundary layers 226A and 226B and the solid films 210.

The second focusing structure 200B or 200 may include a material having an atomic number higher than carbon. The second focusing structure 200B or 200 may include, for example, aluminum (Al), titanium (Ti), silicon (SiO2), or zinc (Zn).

In exemplary embodiments, the second focusing structure 200B or 200 may be extracted from a natural object. For example, the second focusing structure 200B or 200 may be extracted from a wing of a morpho butterfly. For example, the epidermis of a wing of a morpho butterfly may have a shape similar to that of the second focusing structure 200B or 200. Therefore, the skin portion may be extracted from the wing of the morpho butterfly and used as the second focusing structure 200B or 200. Forming the second focusing structure 200B or 200 may include extracting the pre-focusing structure from the natural object and performing a process of changing the material of the pre-focusing structure. The process of modifying the material of the pre-focusing structure may be, for example, an anodic oxidation process. For example, the second focusing structure 200B or 200 may include Al2O3, TiO2, SiO2, and ZnO.

When the second focusing structure 200B or 200 is irradiated with a laser, the first focusing structure 200B or 200 may be converted into a plasma layer. The free electrons in the plasma layer may have a near-critical electron density. Thus, the laser may pass through the plasma and may be focused.

The first and second sub-boundary layers 226A and 226B are uniformly distributed in the second focusing structure 200B or 200 to uniformly distribute the free electrons in the plasma layer. Thus, the laser may be focused to the maximum.

In the exemplary embodiments, as shown in FIG. 6, the second focusing structure 200B or 200 may further include a metal film 228 covering the second pore sections 220B and the boundary layer 222. The metal film 228 may include a material having an atomic number higher than carbon. The metal film 228 may include, for example, gold (Au) or silver (Ag). The metal film 228 may increase the energy of charged particles generated by reducing the movement of the elements in the second focusing structure 200B or 200 when charged particles are generated.

Figure 7:
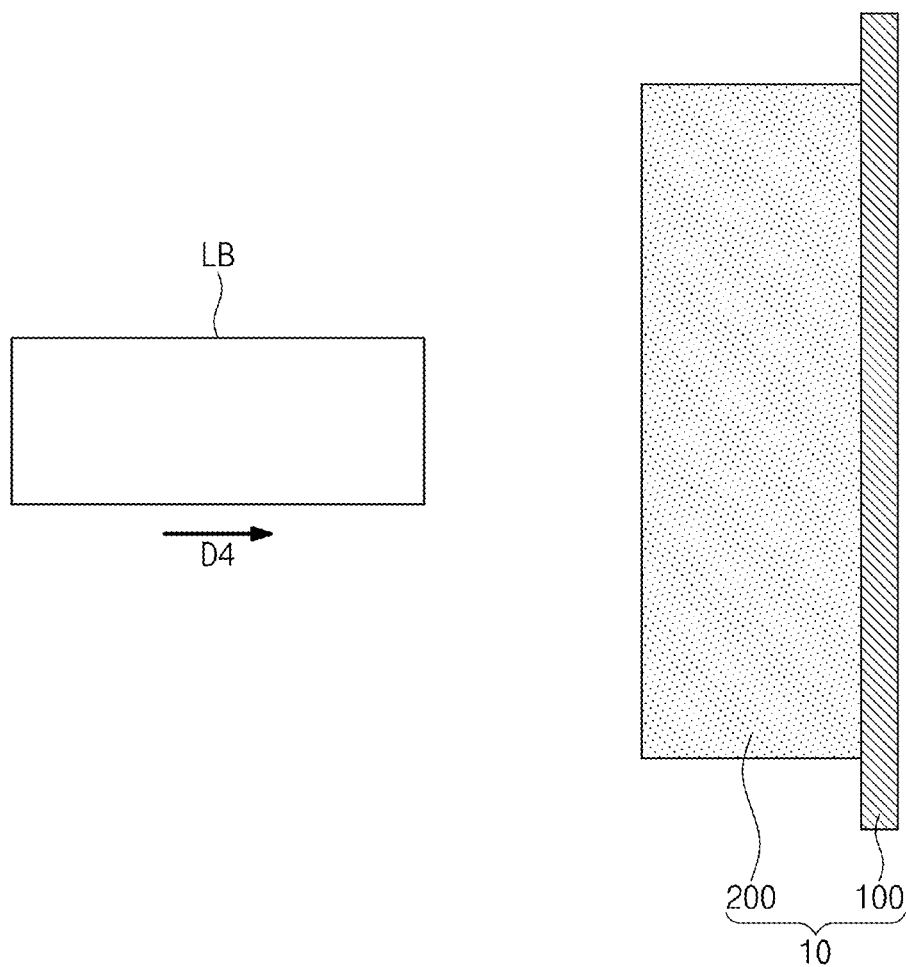
FIGS. 7 and 8 are conceptual diagrams for explaining a laser focusing process according to exemplary embodiments of the inventive concept.
Figure 8:
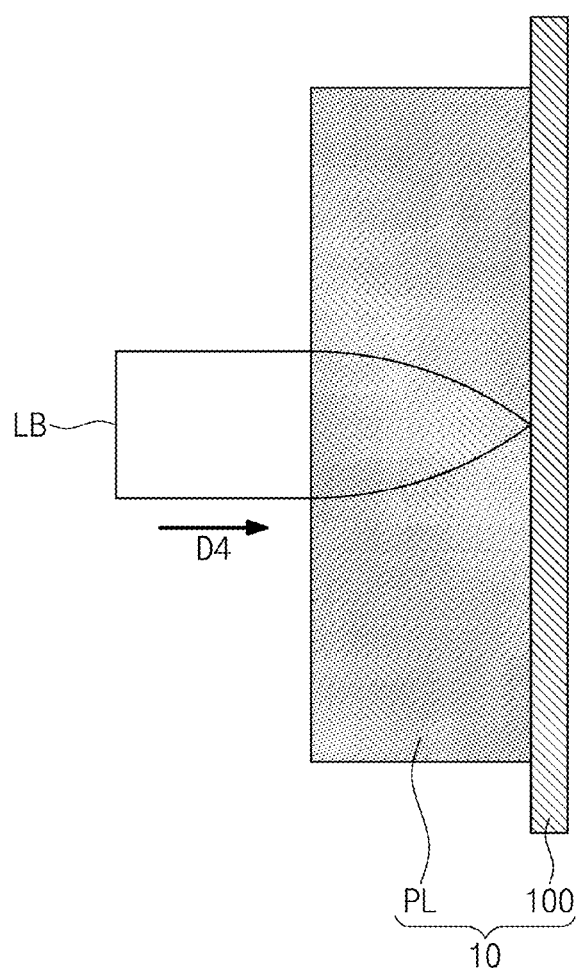

FIGS. 7 and 8 are conceptual diagrams for explaining a laser focusing process according to exemplary embodiments of the inventive concept. For conciseness of description, contents substantially identical to the contents described with reference to FIGS. 1 to 6 are not described.

Referring to FIG. 7, the laser LB may travel toward the target unit 10 in the fourth direction D4. The target unit 10 may be substantially the same as the target unit described with reference to FIGS. 1 to 6. The laser LB may travel toward the upper surface (i.e., the first surface) of the target unit 10.

The laser LB may have a spatially Gaussian shape. In other words, from the viewpoint of viewing the laser LB from the front, the energy of the laser LB may be in the form of a Gaussian graph that becomes smaller from the center of the laser LB toward the outer periphery.

Referring to FIG. 8, the laser LB may travel into the target unit 10 (FIG. 7) and convert the focusing structure (200 in FIG. 7) of the target unit 10 (10 in FIG. 7) into the plasma layer PL. The plasma layer PL may include ions (not shown) and free electrons (not shown). The free electrons may be distributed to have a near-critical electron density. The laser LB may be self-focused by interaction with the free electrons while advancing inside the plasma layer PL. The self-focusing is achieved as laser travels in the plasma layer PL. Hereinafter, self focusing will be briefly described.

When the laser LB travels inside the plasma layer PL, the free electrons may be pushed to the outer portion of the laser LB by interaction with the laser LB. At this time, the force received by the free electrons may be a fondermotive force generated by the interaction. Accordingly, the density of the free electrons in the outer portion of the laser LB may be higher than the density of the free electrons in the central portion of the laser LB. The phase speed of the laser LB traveling in the plasma layer PL may be relatively fast in a high density region of the free electrons and relatively slow in a low density region of free electrons. Therefore, the phase speed of the outer portion of the laser LB may be faster than the phase speed of the central portion of the laser LB. Thus, the laser LB may be self-focused.

Figure 9:
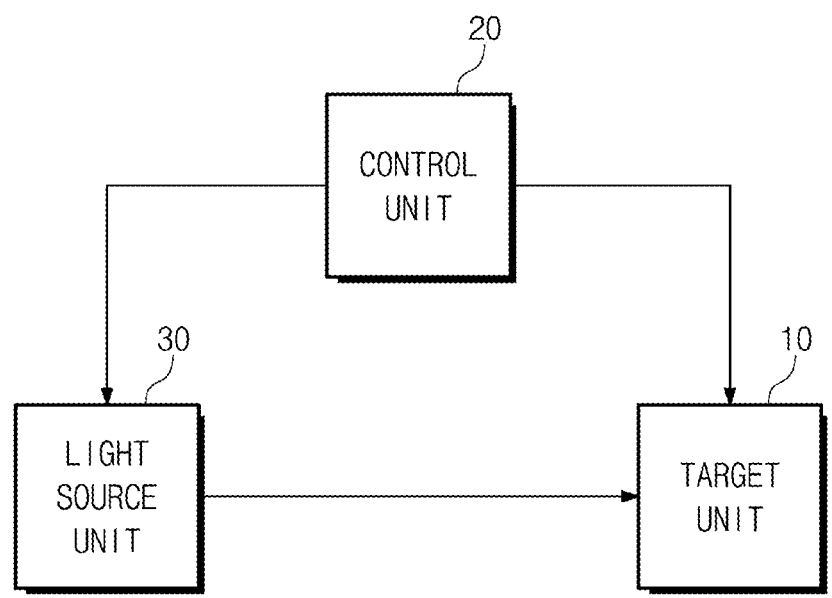
FIG. 9 is a block diagram illustrating a charged particle generation device according to exemplary embodiments of the inventive concept.
Figure 10:
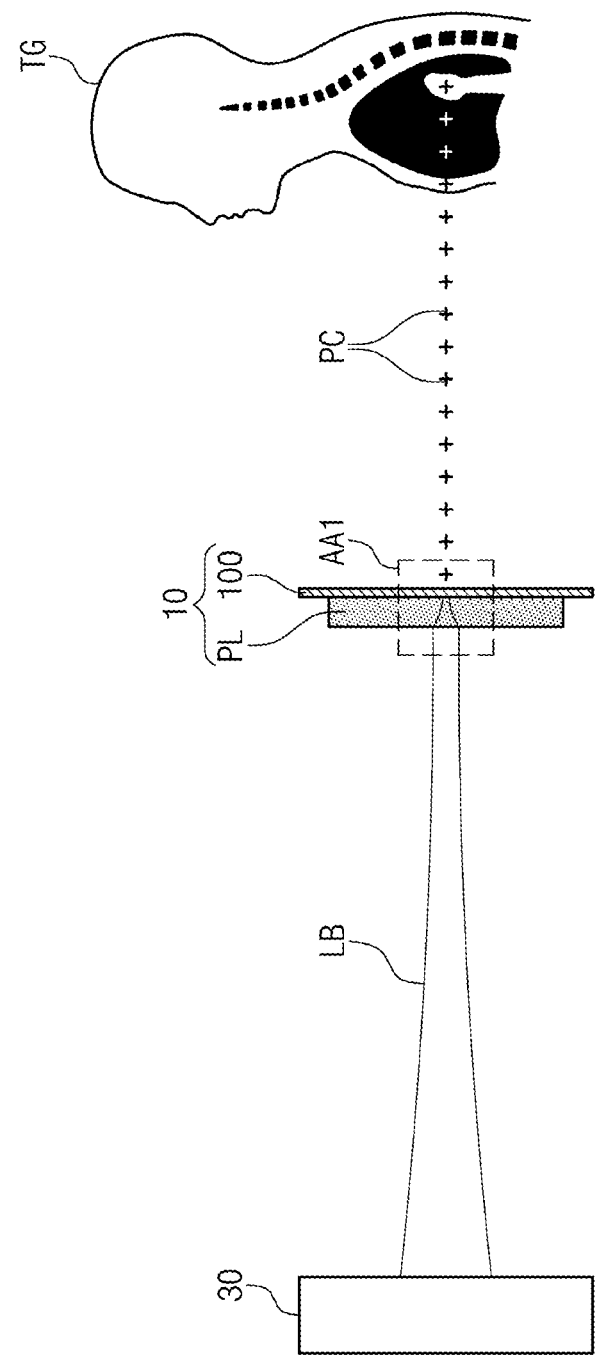
FIG. 10 is a conceptual diagram of a charged particle generation device according to exemplary embodiments of the inventive concept.
Figure 11:
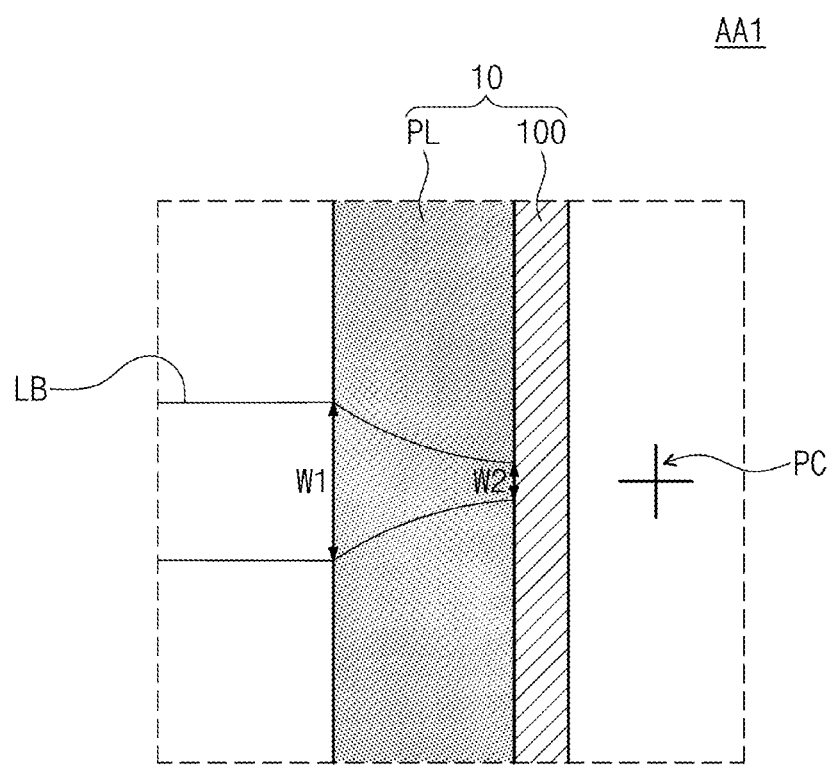
FIG. 11 is an enlarged view of a portion AA1 in FIG. 10.

FIG. 9 is a block diagram illustrating a charged particle generation device according to exemplary embodiments of the inventive concept. FIG. 10 is a conceptual diagram of a charged particle generation device according to exemplary embodiments of the inventive concept. FIG. 11 is an enlarged view of a portion AA1 in FIG. 10. For conciseness of description, contents substantially identical to the contents described with reference to FIG. 1 are not described.

Referring to FIGS. 9 to 11, a charged particle generation device including a light source unit 30, a control unit 20, and a target unit 10 may be provided. The light source unit 30 may be controlled by the control unit 20 to emit the laser LB toward the target unit 10. For example, the light source unit 30 may emit a pulse laser. The laser LB may have the form of a Gaussian beam. Accordingly, the diameter of the laser LB may be the smallest at the focal point of the laser LB and may become larger as the focal point of the laser LB is away from the focal point of the laser LB.

The target unit 10 may be substantially the same as the target unit 10 described with reference to FIG. 1. As described with reference to FIGS. 7 and 8, the focusing structure 200 may focus the laser LB and provide it to the target layer 100. For example, a laser LB having a first diameter W1 may be focused by the focusing structure 200 to form a second diameter W2 less than the first diameter W1 at the upper surface of the target layer 100. The target layer 100 may receive a laser LB having the second diameter W2 to emit charged particles PC. The charged particles PC may be emitted toward the target TG. For example, the target TG may be human.

In the exemplary embodiments, the control unit 20 controls the relative positions of the light source unit 30 and the target unit 10 so that the upper surface of the focusing structure 200 is disposed in a rayleigh range around the focal point of the laser LB. However, this is an exemplary one.

According to the inventive concept, the charged particle generation device may generate charged particles PC having high energy by using the focusing of the laser LB without using a method of increasing the output of the laser. Since charged particles PC with high energy may be generated without increasing the output of the laser, charged particle generation efficiency may be improved. Since no additional devices are required to increase the output of the laser, the cost of generating charged particles may be reduced.

Figure 12:
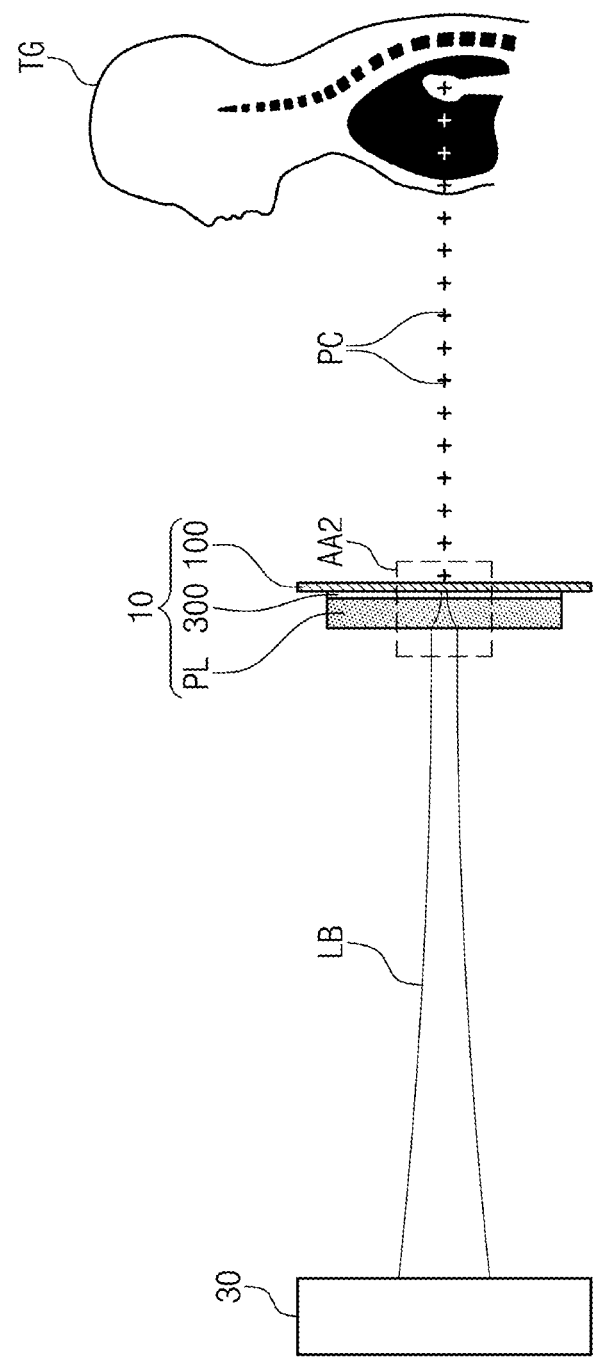
FIG. 12 is a conceptual diagram of a charged particle generation device according to exemplary embodiments of the inventive concept.
Figure 13:
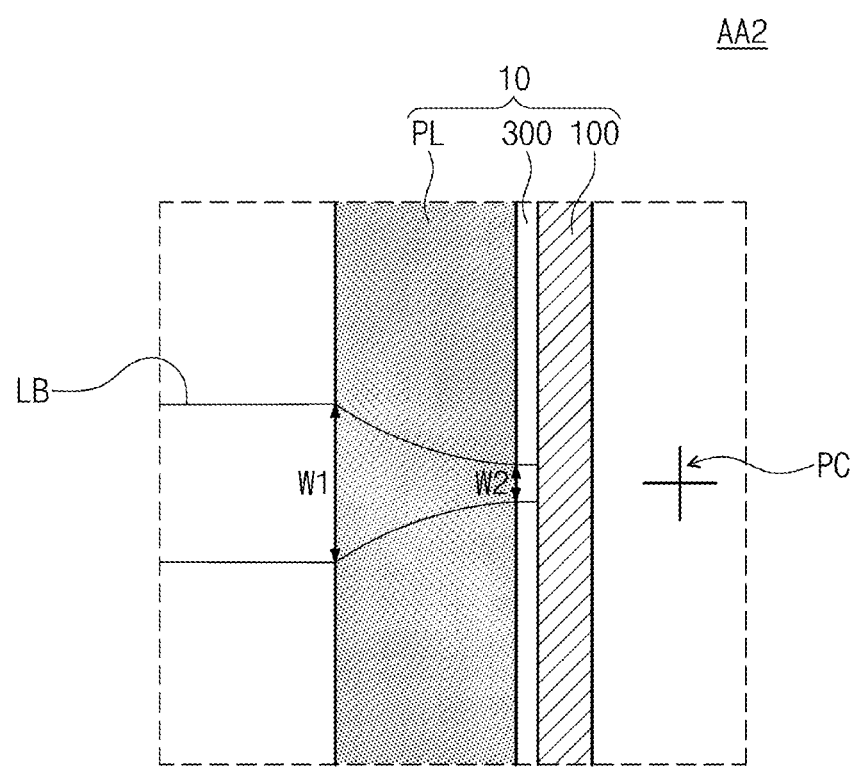
FIG. 13 is an enlarged view of a portion AA2 in FIG. 12.

FIG. 12 is a conceptual diagram of a charged particle generation device according to exemplary embodiments of the inventive concept. FIG. 13 is an enlarged view of a portion AA2 in FIG. 12. For conciseness of description, contents substantially identical to the contents described with reference to FIGS. 9 to 11 are not described.

Referring to FIGS. 12 and 13, a matching layer 300 may be provided between the focusing structure 200 and the target layer 100. The matching layer 300 may reduce the refractive index difference between the plasma layer PL and the target layer 100, thereby reducing the energy loss of the laser LB generated between the plasma layer PL and the target layer 100. For example, the refractive index of the matching layer 300 may have a value between the refractive index of the plasma layer PL and the refractive index of the target layer 100.

According to the inventive concept, since the energy loss of the laser LB is reduced, the charged particle generation efficiency may be improved.

Referring again to FIGS. 7, 8, and 10, the target unit 10 may receive the laser LB and generate charged particles PC. At this time, the energy of the charged particles PC generated depending on the material constituting the focusing structure 200 may be changed.

Charged particles PC may be positive ions generated by Target Normal Sheath Acceleration (TNSA). Specifically, as the laser LB is irradiated on the first surface of the target layer 100, the target layer 100 may be locally ionized. Electrons generated by ionization may be accelerated by electromagnetic interactions with the laser to form electron clouds on the second surface of the target layer 100. Heavier protons and cations compared to electrons may not be instantaneously reacted and are located in the original place and then, may be accelerated by electromagnetic interactions with electron clouds. That is, charged particles PC may be generated by electrical forces generated by electron clouds and charge separation. At this time, other cations other than charged particles PC may interfere with the proton acceleration. When the focusing structure 200 includes an element having an atomic number higher than carbon, the movement of other cations other than the charged particles PC in the target layer 100 may be minimized. Thus, the electrical force by ion separation may be concentrated on the acceleration of charged particles PC, and the energy of charged particles PC may be increased.

According to the inventive concept, the efficiency of charged particle generation may be maximized.

According to the inventive concept, the cost of increasing the energy of a charged particle may be minimized.

However, the effect of the inventive concept is not limited to the above disclosure.

Although the exemplary embodiments of the inventive concept have been described, it is understood that the inventive concept should not be limited to these exemplary embodiments but various changes and modifications can be made by one ordinary skilled in the art within the spirit and scope of the inventive concept as hereinafter claimed.

What is claimed is:

1. A charged particle generation device comprising:
a light source unit configured to emit a laser;
a target layer that receives the laser and emits charged particles; and
a focusing structure disposed on the target layer to focus the laser,
wherein the focusing structure comprises:
solid films extending on an upper surface of the target layer in a direction away from the target layer; and
a pore section disposed between the solid films and having a porous structure,
wherein the focusing structure comprises a material having a higher atomic number than carbon.

2. The charged particle generation device of claim 1, wherein the focusing structure comprises aluminum (Al) or zinc (Zn).

3. The charged particle generation device of claim 1, wherein the focusing structure further comprises a metal film surrounding the solid films and the pore section, wherein the metal film comprises a material having a higher atomic number than carbon.

4. The charged particle generation device of claim 1, wherein the solid films are arranged along a first direction parallel to the upper surface of the target layer and each of the solid films extends in a second direction intersecting with the first direction.

5. The charged particle generation device of claim 1, wherein the pore section comprises a plurality of pores and a boundary layer surrounding the pores, and the boundary layer has a mesh shape.

6. The charged particle generation device of claim 1, wherein the pore section comprises a plurality of pores and a boundary layer surrounding the pores,
   wherein the boundary layer comprises first sub-boundary layers and second sub-boundary layers each protruding from one side wall and the other side wall of each of the solid films,
   wherein the first sub-boundary layers are arranged in a third direction perpendicular to the upper surface of the target layer,
   wherein the second sub-boundary layers are arranged in the third direction, and each of the second sub-boundary layers is disposed between the first sub-boundary layers.

7. A target unit comprising:
   a target layer having a first surface for receiving a laser and a second surface for emitting charged particles;
   solid films extending from the first surface of the target layer in a direction away from the target layer; and
   a pore section disposed between the solid films and having a porous structure,
   wherein the solid films are arranged along a first direction parallel to the first surface of the target layer, each of the solid films extending in a second direction intersecting with the first direction,
   wherein the solid films and the pore section comprise a material having a higher atomic number than carbon.

8. The target unit of claim 7, wherein the solid films and the pore section comprise aluminum (Al) or zinc (Zn).

9. The target unit of claim 7, further comprising a metal film surrounding the solid films and the pore section, wherein the metal film comprises a material having a higher atomic number than carbon.

10. The target unit of claim 7, wherein the pore section comprises a mesh-shaped boundary layer connecting two solid films adjacent to each other among the solid films and a plurality of pores defined by the boundary layer.

11. The target unit of claim 7, wherein the solid films comprise a first solid film and a second solid film adjacent to each other,
   wherein the pore section comprises first sub-boundary layers protruding from the first solid film toward the second solid film and second sub-boundary layers protruding from the second solid film toward the first solid film,
   wherein the first sub-boundary layers and the second sub-boundary layers are alternately arranged along a direction away from the target layer.

* * * * *